United States Patent
Saakian

(10) Patent No.: US 9,943,493 B2
(45) Date of Patent: Apr. 17, 2018

(54) [2.2.2] BICYCLIC DERIVATIVES AND METHODS OF USE

(71) Applicant: ASE PHARMACEUTICALS, LLC, Naples, FL (US)

(72) Inventor: Susanna A. Saakian, Moscow (RU)

(73) Assignee: ASE Pharmaceuticals, LLC, Naples, FL (US)

( * ) Notice: Subject to any disclaimer, the term of this patent is extended or adjusted under 35 U.S.C. 154(b) by 0 days.

(21) Appl. No.: 15/265,983

(22) Filed: Sep. 15, 2016

(65) Prior Publication Data

US 2017/0000750 A1  Jan. 5, 2017

Related U.S. Application Data

(63) Continuation of application No. 13/140,259, filed as application No. PCT/US2009/068920 on Dec. 21, 2009, now abandoned.

(60) Provisional application No. 61/139,562, filed on Dec. 20, 2008.

(51) Int. Cl.
*A61K 31/19* (2006.01)
*A61K 31/46* (2006.01)

(52) U.S. Cl.
CPC ............. *A61K 31/19* (2013.01); *A61K 31/46* (2013.01)

(58) Field of Classification Search
CPC ..................................................... A61K 31/19
See application file for complete search history.

(56) References Cited

FOREIGN PATENT DOCUMENTS

WO   WO 99/23056   *   3/1998

OTHER PUBLICATIONS

Blumer et al. (Epilepsy & Behavior 5, (2004), 826-840).*
Ledford (Nature, published online May 28, 2008).*
Rao (Epilepsia, 34(2), 347-354, 1993).*
Zoons et al. (Neurology, 2109-2115).*
Kalimullina et al. (Uspekhi Fiziologicheskikh Nauk, 31, 4, English translation, 2000).*
WO 99/23056—Saakian, English translation, 1998.*

* cited by examiner

*Primary Examiner* — Umamaheswari Ramachandran
(74) *Attorney, Agent, or Firm* — Stanley A. Kim

(57) ABSTRACT

Administration of a salt of bi-cyclo [2.2.2] octane-2-carbonic acid reduces dysphoria in dysphoric subjects, ameliorates ethanol craving in alcoholics, reduces the erythrocyte sedimentation rate and the level of liver function markers (AST, ALT, and bilirubin) in human subjects, and reduces the number or strength of seizures in epileptics.

7 Claims, No Drawings

[2.2.2] BICYCLIC DERIVATIVES AND METHODS OF USE

CROSS-REFERENCE TO RELATED APPLICATIONS

The present application is a continuation application of U.S. patent application Ser. No. 13/140,259 filed on Jun. 16, 2011 as a U.S. national phase under 35 U.S.C. 371 of international application number PCT/US09/068920, filed Dec. 21, 2009, which designated the U.S. and claims the priority of U.S. provisional patent application Ser. No. 61/139,562 filed on Dec. 20, 2008, which are incorporated herein by reference in their entirety.

STATEMENT AS TO FEDERALLY SPONSORED RESEARCH

Not applicable.

FIELD OF THE INVENTION

The invention relates generally to the fields of organic chemistry, drug development, pharmacology, and medicine. More particularly, the invention relates to modulating human physiology by administration of one or more [2.2.2] bicyclic derivatives.

BACKGROUND

Developing new drugs to treat human diseases is often based on identifying chemical compounds that exert a beneficial effect on one or more human physiological processes. Those compounds that prevent or reduce disease-associated processes without causing serious toxicity are promising candidates for new drugs. In conventional pharmaceutical development, new or old compounds that might be suitable for use as drugs are first tested in in-vitro assays and/or animal models for both beneficial effects and adverse reactions. The vast majority of compounds tested are discarded at this stage for not being effective or suitable for administration to human subjects (e.g., due to toxicity, instability, or poor pharmacokinetics). Of those few candidates that overcome this first hurdle, only a small fraction are ever approved as drugs for human use because most fail to meet the safety and efficacy requirements required by governmental regulatory bodies. Because of this, it currently costs about $800 million and takes several years time to bring a new drug to market. Accordingly, the value of compounds that show promise of becoming new drugs increases considerably once they are shown to be safe and efficacious in early stage human trials.

SUMMARY

The invention is based on the discovery that a salt of bicyclo [2.2.2] octane-2-carbonic acid exhibits numerous beneficial effects in human beings with few significant side effects. In particular, as described in more detail below, human clinical trials of sodium bicyclo-[2.2.2]-octane-2-carboxylate showed that it was effective in reducing dysphoria in dysphoric subjects, ameliorating ethanol craving in alcoholics, reducing the erythrocyte sedimentation rate and the level of liver function markers (AST, ALT, and bilirubin) in subjects, and reducing the number or strength of seizures in epileptics—all without causing any serious side effects.

Thus salts of salt of bi-cyclo [2.2.2] octane-2-carbonic acid and derivatives thereof offer exciting potential for new drugs.

Accordingly, the invention features a method for treating and/or preventing dysphoria in a human subject by administering to the subject an amount of sodium bicyclo-[2.2.2]-octane-2-carboxylate effective to reduce dysphoria in the subject.

In another aspect, the invention features a method for treating ethanol addiction in a human subject by administering to the subject an amount of sodium bicyclo-[2.2.2]-octane-2-carboxylate effective to reduce ethanol craving in the subject.

In addition, the invention features a method for reducing the level of a liver function marker such as AST, ALT, and bilirubin in a human subject by administering to the subject an amount of sodium bicyclo-[2.2.2]-octane-2-carboxylate effective to the reduce the level of that liver function marker in the subject.

The invention also features a method for reducing the erythrocyte sedimentation rate in a human subject by administering to the subject an amount of sodium bicyclo-[2.2.2]-octane-2-carboxylate effective to the reduce the erythrocyte sedimentation rate in the subject.

Further still, the invention features a method for reducing and/or preventing the number or strength of seizures in a human subject suffering from epilepsy by administering to the subject an amount of sodium bicyclo-[2.2.2]-octane-2-carboxylate effective to reduce the number or strength of seizures in the subject.

In the foregoing methods, the sodium bicyclo-[2.2.2]-octane-2-carboxylate can be administered to the subject in a dose of at least 400 or 600 mg per day, orally, in tablet form, and/or for at least until the desired effect is achieved (e.g., the dysphoria is reduced, for at least 60 days, at least one symptom of the epilepsy is reduced, the ethanol craving is reduced, the level of a liver function marker is reduced, the erythrocyte sedimentation rate is reduced, and/or the number or strength of seizures is reduced).

In the foregoing methods, the human subject can one being treated with at least one anti-seizure drug other than sodium bicyclo-[2.2.2]-octane-2-carboxylate (e.g., Depakin. Carbamazepine, Lamictal, Benzonal, Finlepsin, Clonazepam, Paglupheral, Finlepsin-Retard, Hexamidine, Tegretol, Topomax, Diphenin, Glycin, Biotredin, and/or combinations of the foregoing.

In another aspect, the invention provides for the use of other [2.2.2] bicyclic derivatives to modulate physiological processes in a subject (animal or human being).

Unless otherwise defined, all technical terms used herein have the same meaning as commonly understood by one of ordinary skill in the art to which this invention belongs. Commonly understood definitions of chemical terms can be found in Oxford Dictionary of Chemistry, John Daintith, ed., Oxford University Press, 2008 and R. T. Morrisson et al., Organic Chemistry, 6th edition, Addison-Wesley Publishing Co.: Boston, Mass., 1992.

The compounds employed in the methods of the present invention may exist in the form of a "prodrug". This term as used herein, refers to a generally inactive form of a drug that is made active after metabolic processes within the body convert it to a usable form. In the present invention prodrugs may include but are not limited to carboxylate, sulfonate, and phosphonate esters of Formula (1).

The term "alkyl", as used herein, refers to molecular units that are mainly comprised of carbon and hydrogen. An alkyl group may be a straight or branched chain containing from 1 to 12 carbon atoms, preferably 1 to 6 carbon atoms, or more preferably 1 to 4 carbon atoms. Simple alkyl groups are methyl, ethyl, propyl, butyl, along with branched isomers such as isopropyl, iso-butyl, and tert-butyl. Specifically included within the definition of "alkyl" are those hydrocarbon chains that are optionally substituted. Suitable substitutions include functional groups such as hydroxyl, alkoxy, alkylamino, and halogen with fluoro being particularly preferred.

The carbon number as used in the definitions herein refers to carbon backbone and carbon branching, but does not include carbon atoms of the substituents, such as alkoxy substitutions and the like.

The term "halo" and "halogen" as used herein, refers to fluoro, chloro, bromo, or iodo.

When any variable occurs more than one time in any constituent or in any formula, its definition in each occurrence is independent of its definition at every other occurrence. Combinations of substituents and/or variables are permissible only if such combinations results in stable compounds.

The term "stereoisomers", as used herein, refers to compounds of the same molecular formula but that differ from the arrangement of their in space. Specific forms of stereoisomers are enantiomers and diastereomers.

The term "N-oxide", as used herein, refers to compounds wherein the basic nitrogen atom of either a heteroaromatic ring or tertiary amine is oxidized to give a quaternary nitrogen bearing a positive formal charge and an attached oxygen atom bearing a negative formal charge.

The phrase "pharmaceutically acceptable salt", as used herein, refers those salts of compounds of the invention that are medicinally effective and safe for use in humans. Suitable base salts include, but are not limited to, aluminum, lithium, sodium, potassium, magnesium, calcium, zinc, and certain ammonium salts. For a review on pharmaceutically acceptable base salts see P. H. Stahl and C. G. Wermuth Handbook of Pharmaceutical Salts (2008), incorporated herein for reference.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

The terms "administer", administering" or "administration", as used herein, refer to either directly administering a compound or composition to a patient, or administering a prodrug derivative or analog of the compound to the patient, which will form an equivalent amount of the active compound or substance within the patient's body.

"Subject" or "Patient" refers to animals, including mammals, preferably humans.

An "effective amount" or "an amount effective to" means an amount adequate to cure or at least partially ameliorate the symptoms of a disease or its complications.

Although methods and materials similar or equivalent to those described herein can be used in the practice or testing of the present invention, suitable methods and materials are described below. All publications mentioned herein are incorporated by reference in their entirety. In the case of conflict, the present specification, including definitions will control. In addition, the particular embodiments discussed below are illustrative only and not intended to be limiting.

DETAILED DESCRIPTION

The invention encompasses [2.2.2] bicyclic derivatives and methods of using such derivatives to modulate physiological processes in a subject (animal or human being). In a preferred arrangement, the invention relates to methods for using a salt of bi-cyclo [2.2.2] octane-2-carbonic acid to exert a beneficial effect in a human subject without significant side effects. Beneficial effects include reducing dysphoria in dysphoric subjects, ameliorating ethanol craving in alcoholics, reducing the erythrocyte sedimentation rate and the level of liver function markers (AST, ALT, and bilirubin) in subjects, and reducing the number or strength of seizures in epileptics. The below described preferred embodiments illustrate adaptation of these methods. Nonetheless, from the description of these embodiments, other aspects of the invention can be made and/or practiced based on the description provided below.

General Methods

Methods involving conventional organic chemistry, medicinal chemistry, pharmaceutical sciences, and drug development techniques are described herein. Such methods are described in: Remington: The Science and Practice of Pharmacy, Lippincott Williams & Wilkins, 21st edition (2005); Drug Discovery and Development, Mukund S. Chorghade (Editor) Wiley-Interscience; 1st edition (2007); The Practice of Medicinal Chemistry, 3rd Edition, Camille Georges Wermuth (Editor) Academic Press; 3rd edition (2008); and Clayden et al., Organic Chemistry, Oxford University Press, 1st edition (2000).

[2.2.2] Bicyclic Derivatives

The present invention provides [2.2.2] bicyclic derivatives and methods of using such derivatives to modulate physiological processes in a subject (animal or human being). In one embodiment, the invention is directed to compounds of formula (1):

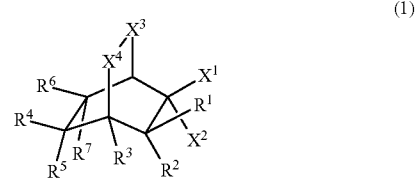

wherein:
$R^1$-$R^8$ are independently selected from the group consisting of H, straight or branched $C_1$-$C_6$ alkyl, $C_2$-$C_6$ alkenyl, $C_2$-$C_6$ alkynyl, $C_2$-$C_8$ cycloalkyl wherein said alkyl, alkenyl, and alkynyl are each optionally substituted with substitutents selected from the group consisting of halogens, hydroxyl, $C_1$-$C_4$ alkoxy, and $C_1$-$C_4$ alkylsulfide; all binary combinations of $R^1$-$R^8$ which are either attached to the same carbon or adjacent carbons on the bicycle skeleton of formula (1) such as $R^1$ and $R^2$ or $R^1$ and $R^3$ and etc. form a $C_3$-$C_8$ cycloalkyl; $R^1$-$R^8$ are independently selected from the group consisting of halogens, hydroxyl, $OR^9$, $SR^9$, $NHR^9$, $NR^9R^{10}$, $ONHR^9$, or $ONR^9R^{10}$; $R^1$-$R^8$ are oligoether tethers of the form O—[($CH_2$)$_m$O]$_n$$R^9$ wherein m is 2-6 and n is 1-6; $X^1$ and $X^2$ are H, $(CR^9R^{10})_nCO_2R^9$, $(CR^9R^{10})_nC(O)SR^9$, $(CR^9R^{10})_nSO_2R^9$, $(CR^9R^{10})_nP(O)(OR^9)(OR^{10})$, wherein n is 0-6, negatively charged groups that form pharmaceutically-acceptable salts which may include but are not limited to oxalate, nitrate, $(CR^9R^{10})_nCO_2^-$, $(CR^9R^{10})_nSO_3^-$, $(CR^9R^{10})_nPO_3^-$, wherein in is 0-6; or $(CR^9R^{10})_nAr^1$; $X^3$ and $X^4$ are O, S, N-oxide, carbonyl, sulfonyl, sulfoxyl, phosphinyl, phosphanyl, $NR^{11}$, or $CR^{11}R^{12}$; $R^9$ and $R^{10}$ are independently selected from the group consisting of H, aryl, heteroaryl, aryl-$CR^{11}R^{12}$, heteroaryl-$CR^{11}R^{12}$, straight or branched $C_1$-$C_6$ alkyl, $C_2$-$C_8$ cycloalkyl wherein said alkyl and cycloalkyl are each optionally substituted with substitutents selected from the group consisting of halogens, aryl, heteroaryl, hydroxyl, $C_1$-$C_4$ alkoxy, and $C_1$-$C_4$ alkylsulfide; $Ar^1$ is independently selected from the group consisting of ortho-, meta-, para-substituted aryl groups including benzoate, benzenesulfonate, benzenephosphonate, salicylate, 2-nicotinate, 3-nicotinate, or para-cinnamate; $R^{11}$ and $R^{12}$ are independently selected from the group consisting of H, straight or branched $C_1$-$C_6$ alkyl, $C_2$-$C_6$ alkenyl, $C_2$-$C_6$ alkynyl, $C_2$-$C_8$ cycloalkyl wherein said alkyl, alkenyl, and alkynyl are each optionally substituted with substitutents selected from the group consisting of halogens, hydroxyl, $C_1$-$C_4$ alkoxy, and $C_1$-$C_4$ alkylsulfide.

In another embodiment, the invention is directed to compositions comprising the compound of formula (1) and one or more or pharmaceutically-acceptable carriers. More particularly, the present invention provides the use of compounds of formula (1) wherein: one of $X^1$ and $X^2$ is hydrogen and the other is carboxylate; $X^3$ and $X^4$ are $CH_2$.

Compounds of Formula (1) may include one or multiple chiral centers leading to stereoisomeric forms. Formula (1) encompasses all possible stereoisomeric forms particularly those that possess the activities discussed herein. These forms include single enantiomers, mixtures of enantiomers, and mixtures of diastereomers. Compounds employed in the present methods may be isolated in optically active or racemic forms. Thus, all chiral, diastereomeric, racemic forms and all geometric isomeric forms of a structure are intended, unless the specific stereochemistry or isomeric form is specifically indicated. Stereoisomers of the compounds of Formula (1) can be selectively synthesized using stereo- and enantio-selective reactions known to those skilled in the art. Alternatively, single isomers may be isolated in pure form using well-known techniques including, but not limited to, recrystallization with chiral and achiral salts, and chromatography with a variety of media including chiral.

The present invention also includes all pharmaceutically acceptable isotopically-labelled compounds of Formula (1) wherein one or more atoms are replaced by with their less common isotope. Examples of isotopes suitable for inclusion in the compounds of the invention include, but are not limited to, isotopes of hydrogen, such as deuterium and tritium, carbon, such as $^{11}C$, $^{13}C$ and $^{14}C$, nitrogen, such as $^{13}N$ and $^{15}N$, oxygen, such as $^{15}O$, $^{17}O$ and $^{18}O$, fluorine, such as $^{18}F$, iodine, such $^{123}I$ and $^{125}I$, and phosphorus, such as $^{32}P$.

Certain isotopically-labelled compounds of Formula (1), for example, those incorporating a radioactive isotope, are useful in studies of drug metabolism and tissue distribution. The radioactive isotopes tritium and carbon-14 are particularly useful for this purpose since they are usually easy to prepare and can be readily detected a low concentrations in the body. Substitution of hydrogen in the compounds of Formula (1) with deuterium is also included in the present invention. Such substitution may lead to greater metabolic stability in the therapeutic compounds of this invention possibly increasing their therapeutic potential. Substitution with positron emitting isotopes, such as $^{11}C$, $^{15}O$ and $^{13}N$, and especially $^{18}F$, can be useful in Positron Emission Topography (PET) medical imaging studies. Such studies are typically used to study drug metabolism and tissue distribution of therapeutic compounds.

The compounds of Formula (1) may be prepared using methods known to those skilled in the art of organic chemistry including the general synthetic pathways indicated below. The specific conditions such as temperature, reagents, solvents, and other variables are those which are suitable for reactions given below and would be readily known to those skilled in the art. Compounds of Formula (1) can be prepared as illustrated in reaction Scheme 1. The bicyclic alkene of Formula (4) can prepared by a Diel-Alder or related [4+2] addition reaction of diene (2) and dienophile (3) usually under heat and pressure. Often these reactions can be performed without solvent. Subsequent addition of compound (5) to the double bond of (4) leads to compound of Formula (1). When $R^5$ and $R^7$ are hydrogen, this addition is know as an hydrogenation reaction and is usually brought about by catalysts such as palladium or platinum.

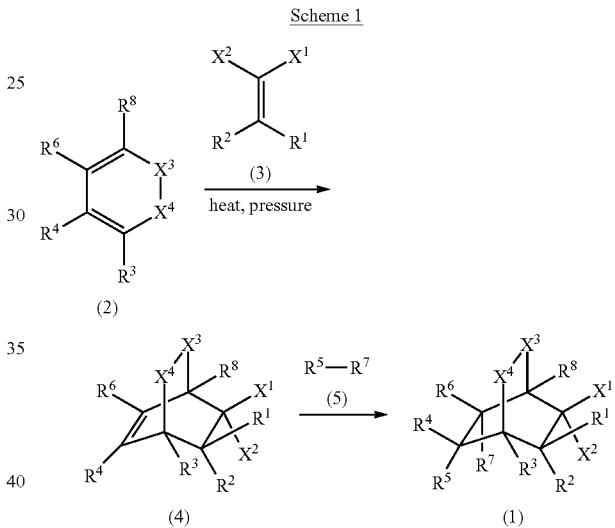

Scheme 1

Pharmaceutically acceptable salts of the compounds of Formula (1) may be prepared by treating the corresponding free acid with one molecular equivalent of a pharmaceutically acceptable base. More particularly, in compounds of Formula (1), when $X^1$ is $CO_2R^9$, hydrolysis to the carboxylic acid is possible as illustrated in Scheme 2. These hydrolysis reactions are usually brought about by treatment with metal hydroxides followed by acidic workup. Subsequent treatment of the carboxylic acid with base such as a metal hydroxide leads to the carboxylate salt ($X^1$=$CO_2M$).

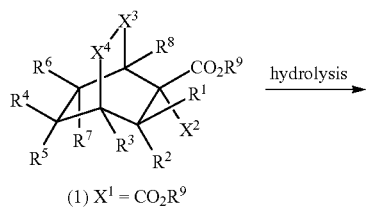

Scheme 2

-continued

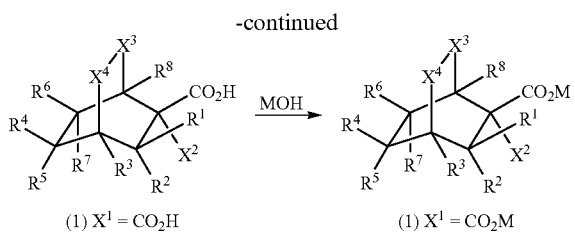

(1) $X^1 = CO_2H$     (1) $X^1 = CO_2M$

The reagents and starting materials described in the above procedures and schemes are either commercially available or readily obtained from known compounds using methods apparent to those skilled in the art of organic chemistry.

The intermediates leading up to the compounds of Formula (1) may be purified by typical procedures such as silica gel chromatography, distillation, recrystallization, or preparative HPLC chromatography using chiral, reversed-phased, or normal phase columns.

Bi-cyclo [2.2.2] Octane-2-Carboxylates

Especially preferred examples of the foregoing compounds are two enantiomeric isomers of formula (1):

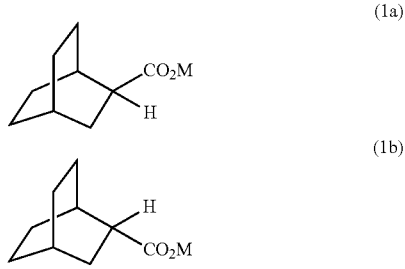

wherein: M is independently selected from the group consisting of: monocations Li, Na, and K; or dications Ca, Mg, and Zn.

Specific embodiments of the present invention include the following compounds of Formula (1), all pharmaceutically-acceptable salts thereof, complexes thereof, and derivatives thereof that convert into pharmaceutically active compound upon administration:

(S)-bicyclo[2.2.2]octane-2-carboxylate lithium salt;
(R)-bicyclo[2.2.2]octane-2-carboxylate lithium salt;
(S)-bicyclo[2.2.2]octane-2-carboxylate sodium salt;
(R)-bicyclo[2.2.2]octane-2-carboxylate sodium salt;
(S)-bicyclo[2.2.2]octane-2-carboxylate potassium salt;
(R)-bicyclo[2.2.2]octane-2-carboxylate potassium salt;
(S)-bicyclo[2.2.2]octane-2-carboxylate calcium (II) salt;
(R)-bicyclo[2.2.2]octane-2-carboxylate calcium (II) salt;
(S)-bicyclo[2.2.2]octane-2-carboxylate magnesium (II) salt;
(R)-bicyclo[2.2.2]octane-2-carboxylate magnesium (II) salt;
(S)-bicyclo[2.2.2]octane-2-carboxylate zinc (II) salt;
(R)-bicyclo[2.2.2]octane-2-carboxylate zinc (II) salt.

Sodium bicyclo-[2.2.2]-octane-2-carboxylate can be prepared by adding 0.2 mole of bicyclo-[2.2.2]-octane-2-carboxylic acid (m. p. 84-86° C.) to a solution of 0.18 mole NaOH or NAHCO$_3$, or 0.9 mole Na$_2$CO$_3$ in the water. After stirring the mixture for 1 hour at room temperature, the excess acid is filtered off or extracted with the organic solvents and the aqueous solution is evaporated dry in vacuum at 120-140° C. to give the sodium salt. The yield is 93%, m.p 440-450° C. with decomposition. The salt has the appearance of white flaked crystals, is weakly hygroscopic, and does not form the stable crystallohydrates. The aqueous solutions have the neutral reaction. The use of pure acid and base in the synthesis yields the salt with 98-99% purity and eliminates the need in the additional purification at the final step of synthesis. The completeness of drying is checked by absence of 3430 cm$^{-1}$ band in the infrared spectrum of salt. The purity is confirmed by the absence of absorption near 3040 cm$^{-1}$ in the infrared spectrum and 6.5-7.0 ppm signals in the nuclear magnetic resonance spectrum. The structural characteristics are the stretching frequencies of carboxylic anion—1570-1554 cm$^{-1}$ and 1420-1411 cm$^{-1}$ doublets in IR spectrum (vaseline oil); 2.42 ppm multiplet, associated with $\alpha$-proton in NMR spectrum (200.13 MHz, D$_2$O); nine signals at 21.72, 23.71 (C$_4$), 24.75, 24.96, 26.03, 27.71 (C$_1$), 29.03, 44.22 and 185.65 (COO$^-$) ppm in the spectrum of carbon NMR (50.31 MHz, D$_2$O). The salt prepared with this method is not optically active.

Magnesium bicyclo-[2.2.2]-octane-2-carboxylate can be prepared by dissolving 0.05 g of activated magnesium with heating in 50 ml of dry methanol under an inert atmosphere. The resulting solution is mixed in portions with 0.1 mole bicyclo-[2.2.2]-octane-2-carboxylic acid in 50 ml of methanol. After stirring the mixture for 1 hour at room temperature, the resulting precipitate is filtered off and dried in vacuum to give the magnesium salt with yield of about 99%. The salt has the appearance of white plates, m.p. 432-436° C. with decomposition. The salt prepared with this method is not optically active.

It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be used to prevent certain functional groups from undergoing undesired reactions. Suitable protecting groups for various functional groups as well as suitable conditions for protecting and deprotecting particular functional groups are well known in the art. See, for example, T. W. Greene and G. M. Wuts, Protecting Groups in Organic Synthesis, Third Edition, Wiley, New York, 1999, and references cited therein.

For compounds containing one or more chiral centers, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley and Sons, 1991), Rodd's Chemistry of Carbon Compounds, Volumes 1-5 and Supplementals (Elsevier Science Publishers, 1989), Organic Reactions, Volumes 1-40 (John Wiley and Sons, 1991), March's Advanced Organic Chemistry, (John Wiley and Sons, 4.sup.th Edition), and Larock's Comprehensive Organic Transformations (VCH Publishers Inc., 1989).

Pharmaceutical Formulations

The compound of formula I and derivatives thereof can be included along with one or more pharmaceutically acceptable carriers or excipients to make pharmaceutical compositions which can be administered by a variety of routes including oral, rectal, transdermal, subcutaneous, intravenous, intramuscular, and intranasal. Suitable formulations for use in the present invention are found in Remington's Pharmaceutical Sciences, Mace Publishing Company, Philadelphia, Pa., (1985).

Typically, the active ingredient is mixed with an excipient, diluted by an excipient, and/or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, sterile liquids for intranasal administration (e.g., a spraying device), and sterile packaged powders. In preparing a formulation, it may be necessary to mill the active compound to provide the appropriate particle size prior to combining with the other ingredients. Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing 25 to about 1200 mg (e.g., 25, 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1100, and 1200 mg unit dosage forms) of the active ingredient.

The active compound is effective over a dosage range and is generally administered in a pharmaceutically effective amount (e.g., 50 to 1200 mg per day per patient or about 1-20 mg/kg per day; or preferably, 400 to 600 mg per day per patient or about 5-8 mg/kg per day). It will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound. Tablets or pills may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Liquid forms may be incorporated for administration orally, buccally, intranasally, or by injection include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles. To enhance serum half-life, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka, et al., U.S. Pat. Nos. 4,235,871, 4,501,728 and 4,837,028 each of which is incorporated herein by reference.

The amount administered to the patient will vary depending upon what is being administered, the purpose of the administration, such as prophylaxis or therapy, the state of the patient, the manner of administration, and the like all of which are within the skill of qualified physicians and pharmacists. In therapeutic applications, compositions are administered to a patient already suffering from a disease in an amount sufficient to cure or at least partially arrest the symptoms of the disease and its complications. Amounts effective for this use will depend on the disease condition being treated as well as by the judgment of the attending clinician depending upon factors such as the severity of the symptoms, the age, weight and general condition of the patient, and the like.

Other active ingredients might also be included in the pharmaceutical compositions, e.g., other neurologically active drugs.

Methods of Use

The invention features methods for treating a patient (e.g., a human subject or an animal such as a dog or cat) having a neurological, psychological, or other disease or disorder by administering to the subject the compound of Formula (1) or a derivative thereof in an amount effective to reduce a symptom of the disease or disorder. For example, dysphoria can be reduced by administering to a subject an amount of the compound of Formula (1) or a derivative thereof effective to reduce dysphoria in the subject. Ethanol addiction can be treated by administering to a subject an amount of the compound of formula I or a derivative thereof to reduce ethanol craving in the subject. Epilepsy can be treated by administering to a subject an amount of the compound of formula I or a derivative thereof effective to reduce the number or strength of seizures in the subject.

In addition, the invention features a method for disease-associated conditions in a subject. For example, the level of a liver function marker such as AST, ALT, and bilirubin can be reduced by administering to a subject an amount of the compound of formula I or a derivative thereof effective to the reduce the level of that liver function marker in the subject. Similarly, the erythrocyte sedimentation rate in a subject can be reduced by administering to the subject an amount of the compound of formula I or a derivative thereof effective to the reduce the erythrocyte sedimentation rate in the subject.

In the foregoing methods, sodium bicyclo-[2.2.2]-octane-2-carboxylate can be administered to the subject in a dose of at least 400 or 600 mg per day, orally, in tablet form, and/or for at least until the desired effect is achieved (e.g., the dysphoria is reduced, for at least 60 days, at least one symptom of the epilepsy is reduced, the ethanol craving is reduced, the level of a liver function marker is reduced, the erythrocyte sedimentation rate is reduced, and/or the number or strength of seizures is reduced).

EXAMPLES

Example 1—Clinical Trials with Sodium bicyclo-[2.2.2]-octane-2-carboxylate

In human clinical trials, sodium bicyclo-[2.2.2]-octane-2-carboxylate was shown to exhibit excellent assimilation without significant negative side effects. Clinical trials involving administration of sodium bicyclo-[2.2.2]-octane-2-carboxylate were performed on 30 epilepsy patients and 20 volunteers in two clinics in Moscow. The subjects in the epileptic group had a variety of forms of epilepsy of different etiology. Classification of the patients was done in accordance with International Classification of Epilepsy and Epileptic Syndromes (ILAE, 1989). Some of the subjects also suffered from addictive disorders (alcoholism, drug addiction). In 73% of trial subjects, sodium bicyclo-[2.2.2]-octane-2-carboxylate administration reduced the frequency, intensity, and duration of epileptic seizures. Sodium bicyclo-[2.2.2]-octane-2-carboxylate showed a particularly antispasmodic effect on patients with the acute form of partial epilepsy. It normalized cerebral blood circulation and increased the sympathetic tonus of the patients. It also suppressed secondary generalization of epileptic seizures, and improved the subjects' mood, working efficiency, and overall sense of good health.

The following were used to assess trial subjects:
Visual checkup
EEG
CT
MRT
Clinical blood and urine tests
general blood test
biochemical blood test
general urine tests
Inspection and checkup of organs and systems:
respiratory system
cardiovascular system
alimentary system
urinary system
Neurological status
Concurrent disease status.

Example 2—Randomized Open-Controlled Study on the Safety, Tolerability, and Effects of Administration of Sodium bicyclo-[2.2.2]-octane-2-carboxylate The study of sodium bicyclo-[2.2.2]-octane-2-carboxylate as an addition to a base therapy was conducted in the group of adult epilepsy patients. Sodium bicyclo-[2.2.2]-octane-2-carboxylate was administered during 10 weeks. Thirty patients in both hospitals (twenty-six males and four females) were included in the studies.

TABLE 1

Patients Demographics.

| Parameter | Males | Females |
| --- | --- | --- |
| Age (years), average | 35 | 32 |
| Weight (kg), average | 71.5 | 60 |
| Height (cm), average | 176 | 165 |
| Disease duration (years) | 3-29 | 3-29 |

Base therapy was administered in accordance with recommendations by the International Anti-epileptic League (1989). During the study, the patients continued to receive pathogenetic treatment. Medication names, doses and the duration of any treatment were registered in patients' medical records (MR). The patients continued receiving their standard prescribed medications and were not switched to a different drug at any time during the study.

Base therapy in pre-sodium bicyclo-[2.2.2]-octane-2-carboxylate phase included the following drugs taken as a single drug or in combinations:
1) Depakin (valproic acid).
2) Carbamazepine (Finlepsin, Tegretol).
3) Lamictal (lamotrigine)+Clonazepam.
4) Depakin+Benzonal (benzonalum).
5) Depakin+Finlepsin.
6) Carbamazepine+Clonazepam.
7) Carbamazepine+Paglupheral.
8) Finlepsin+Benzonal.
9) Finlepsin-Retard+Hexamidine.
10) Tegretol+Topomax (topiramate).
11) Diphenin (phenytoin)+Glycin.
12) HexamidinE+Finlepsin.
13) Biotredin+Glycin.
14) Glycin+Carbamazepine.

During the introductory period of 7 to 10 days, the patients were examined; base therapy scheme was being finalized and was described in a standard protocol. In accordance with the protocol, the patients were screened for inclusion/exclusion factors. Only those patients who signed an informed consent and who satisfied the inclusion criteria were included in the study. The frequency of epileptic seizures in patients receiving pre-sodium bicyclo-[2.2.2]-octane-2-carboxylate base therapy varied from 1 to 16 times a month.

At the start of sodium bicyclo-[2.2.2]-octane-2-carboxylate protocol, all patients began receiving sodium bicyclo-[2.2.2]-octane-2-carboxylate at 100 mg four times a day. If the clinical effect was absent by day 14, the dose of Sodium bicyclo-[2.2.2]-octane-2-carboxylate was increased to 150 mg. Patients with various forms of epilepsy were selected for the study (Table 2).

TABLE 2

Patient groups.

| | Epilepsy Form | # of Patients |
|---|---|---|
| Generalized Epilepsy | With isolated generalized seizures | 5 |
| Partial Epilepsy | With simple partial secondary-generalized seizures | 4 |
| | With complex partial secondary-generalized seizures | 12 |
| | With polymorphic seizures | 9 |

As can be seen in Table 2, five patients were diagnosed with idiopathic generalized epilepsy with isolated generalized seizures. The remaining patients suffered from partial epilepsy with simple or complex symptoms. In this group, four patients were diagnosed with simple partial and secondary-generalized seizures, twelve patients had complex partial secondary-generalized seizures, and nine patients suffered from polymorphic seizures.

In some patients, an obvious connection existed between the seizures and past cranio-cerebral trauma suffered, which was confirmed by imaging (CAT scan, MRI). In one of the patients, the onset of seizures was preceded by open cranio-cerebral trauma (fracture of the frontal bone accompanied by damage of frontal sinuses). This patient underwent plastic surgery.

On CAT scans and MRI tomograms, various posttraumatic changes (posttraumatic cysts, posttraumatic atrophic changes, signs of posttraumatic encephalopathy and hypertension syndrome) were detected. In four patients, the onset of epileptic seizures followed neuro-infection. In two patients, partial epilepsy of mixed and complex genesis with seizureless paroxysm was diagnosed. In the remaining patients, complex-partial and secondary-generalized seizures developed on the background of chronic toxic polyneuropathy and toxic degeneration of a nervous system.

The structure of the patients group with partial epilepsy is summarized below.

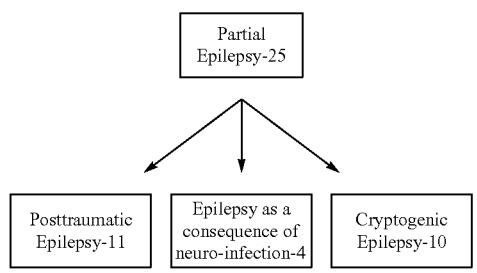

To enforce the therapy schedule, medications were passed to the patients directly by the research physician, and administration dates and doses were recorded in study documentation and in the patients' medical records (MRs). Comprehensive information about patients and their current medical conditions was recorded in patients' MRs regardless of the relevance of this information to the study.

During each scheduled visit and at the completion of the study, complete physical examination of each patient was performed. Physical exams included patients' general condition, examinations of the skin, ENT, lungs, heart, stomach, lymph nodes, central nervous system, etc. Valid data obtained before beginning of Sodium bicyclo-[2.2.2]-octane-2-carboxylate treatment was entered in appropriate sections of MRs. The data collected during the treatment (including the observed side effects) was entered in the Brief Description sections of the MRs.

Main study parameters included efficiency criteria such as the number and severity of seizures, and safety criteria such as the clinical and laboratory tests. The complete examination included:
1) Neurological exams.
2) Computer-assisted tomography (CAT scan).
3) MRI of the brain.
4) General blood work: baseline before Sodium bicyclo-[2.2.2]-octane-2-carboxylate treatment, 2 weeks and 1.5 months after the beginning of the treatment.
5) General urine analysis.
6) Blood biochemistry.
7) ECG.
8) EEG and pharmaco-EEG.

Physical exams and testing results were registered by a research physician in the MRs and were analyzed by statistical methods.

The study drug was sodium bicyclo-[2.2.2]-octane-2-carboxylate at a 50 mg dose formulated as a white tablet weighing 0.2 g. The maximum storage time allowed was 3 years. The drug was stored in dry, cool place protected from light, at a maximum temperature of 25° C.

Analysis of the results showed that sodium bicyclo-[2.2.2]-octane-2-carboxylate was an efficient anti-epileptic drug lacking significant side effects. The effective therapeutic dose was determined as 400 mg per day in 60% of the patients, and 600 mg per day in the remaining 40%. Safety aspects of sodium bicyclo-[2.2.2]-octane-2-carboxylate were evaluated during the treatment and after the treatment by monitoring the clinical and laboratory parameters. No unfavorable effects of Sodium bicyclo-[2.2.2]-octane-2-carboxylate on the blood counts and blood biochemistry were observed (see Tables 3 and 4).

TABLE 3

General blood work data.

| | Erythrocytes | | Hemoglobin | | Color Index | | Platelets | | Leukocytes | |
|---|---|---|---|---|---|---|---|---|---|---|
| | Before | After | Before | After | Before | After | Before | After | Before | After |
| Average | 4.75 | 4.79 | 143.4 | 140.13 | 0.895 | 0.928 | 205.5 | 230.3 | 7.9 | 7.47 |
| % dev. | 1.48 | | 2.3 | | 3.7 | | 12.07 | | 5.95 | |

| | Lymphocytes (%) | | Monocytes (%) | | Neutrophiles (%) | | Eosinophiles (%) | | ESR, mm | |
|---|---|---|---|---|---|---|---|---|---|---|
| | Before | After | Before | After | Before | After | Before | After | Before | After |
| Average | 20.9 | 21.1 | 3.0 | 2.8 | 72.7 | 71.2 | 2.53 | 2.53 | 7.3 | 5.2 |
| % dev. | 0.94 | | 6.7 | | 2.06 | | 0 | | 28.8 | |

TABLE 4

Blood chemistry data.

| | General Protein | | Glucose | | ACT | | ALT | | General bilirubin | | Creatinin | |
|---|---|---|---|---|---|---|---|---|---|---|---|---|
| | Before | After | Before | After | Before | After | Before | After | Before | After | Before | after |
| Average | 75.5 | 77.4 | 4.75 | 4.48 | 45.1 | 24.6 | 46.2 | 21.5 | 14.3 | 11.5 | 70.5 | 69.4 |
| % dev. | 2.5 | | 5.7 | | 45.4 | | 53.5 | | 19.6 | | 1.6 | |

Before—before Sodium bicyclo-[2.2.2]-octane-2-carboxylate treatment

After—after Sodium bicyclo-[2.2.2]-octane-2-carboxylate treatment.

No statistically significant differences in any other parameters before and after Sodium bicyclo-[2.2.2]-octane-2-carboxylate treatment were detected.

To evaluate treatment efficacy, the frequency and severity of epileptic seizures were monitored. Treatment by Sodium bicyclo-[2.2.2]-octane-2-carboxylate resulted in weakening of the seizures and decreasing their frequency from 2 to 2.5 times. Decrease in seizure frequency was observed in 22 patients (73.3%). In the majority of patients suffering from partial epilepsy, seizures became less severe and occurred less frequently. The patients reported feeling better, with improvement of mood, work efficiency, and sleep quality. During the six week period of treatment by sodium bicyclo-[2.2.2]-octane-2-carboxylate, patients suffering from the encephalopathy of mixed etiology and from symptomatic partial epilepsy with complex-partial secondary generalized convulsive seizures developed only rare complex-partial seizures accompanied by automatic movements and scratching without secondary generalization.

Some patients did not show noticeable improvement during six weeks of treatment by Sodium bicyclo-[2.2.2]-octane-2-carboxylate. Two patients with hydrocephaly and diffuse atrophy in the brain (KT) and suffering from symptomatic partial epilepsy did not demonstrate any improvement. In another patient, the type, duration and frequency of seizures did not change during 1.5 month of treatment. This patient suffered from the consequences of prenatal pathology and had symptomatic partial epilepsy. MRI revealed structural scarring and atrophic changes in the brain. In five patients with partial epilepsy, the frequency of seizures remained unchanged. However, the seizures in these patients became shorter and less severe, these patients reported feeling better, having better mood, work efficiency, and sleep quality.

Importantly, in the patients who suffered from alcohol addiction in the past, dysphoria and paroxysmal activity on EEG disappeared or decreased after 1.5 month of treatment by sodium bicyclo-[2.2.2]-octane-2-carboxylate. This effect correlated with disappearance of alcohol addiction.

Investigation of sodium bicyclo-[2.2.2]-octane-2-carboxylate effect on EEG parameters revealed the following:
1) The frequency of epileptic seizures was decreased.
2) The absolute number of electrophysiological complexes and their diversity (pike-waves, spike-waves, or sharp wave-slow wave) was decreased during and after phono-stimulation.
3) Depression of an α-rhythm was decreased.
4) Localization signs of β-, δ-, and θ-activities disappeared.
5) Meaningful changes occurred upon phono-stimulation.
6) Localized activity upon hyper-ventilation decreased.

The averaged changes in EEG parameters are summarized in Table 5.

TABLE 5

| EEG parameters (focus of pathological activity), μV | Before treatment | 197.7 |
|---|---|---|
| | After treatment | 151.5 |

Based on visual evaluation and spectrum power analysis of EEG from epilepsy patients allowed identifying three main groups of the patients according to their EEG type. In patients of the first group, EEG had regional differences and displayed fragmented and weakly modulated α-rhythm. In the patients of the second group, the EEG was disorganized in the base rhythm. In the patients of the third group, the EEG had no α-rhythm and had bio-electrical activity with low amplitude.

To evaluate the coherence of distinctive frequency components on EEG from different regions of the brain, computation of a complex coherence function (COH) was performed. This method allows studying statistical linear links of electrical processes in two different regions of the brain and evaluating them based on the linkage value on each separate frequency, regardless of the amplitude. According to the type of electrical activity in the brain, the coherence analysis was performed by EEGs classified into the groups described above.

In the patients of the first group, EEG showed regional differences, as well as the fragmented and weakly modulated α-rhythm. After 1.5 month of treatment by sodium bicyclo-[2.2.2]-octane-2-carboxylate, the intra-hemispheric connections decreased on both right and left sides. Decreasing of short inter-hemispheric connections was also noticed, and α-rhythm COH values decreased in the front-central area. In the majority of patients of the second group, stable clinical effect was achieved. During the treatment, the decrease of α-rhythm- and θ-rhythm-COH values for intra-hemispheric and short inter-hemispheric connections was seen, which reached its maximum by the end of 1.5 month period of Sodium bicyclo-[2.2.2]-octane-2-carboxylate treatment. In the patients of the third group that exhibited a "flat" type of bio-electric activity, single administration of sodium bicyclo-[2.2.2]-octane-2-carboxylate caused a decrease of COH values of δ- and θ-activities for intra-hemispheric connections (at the focus), which reached its maximum by the end of 1.5 month period of sodium bicyclo-[2.2.2]-octane-2-carboxylate treatment.

During the treatment period, inter-hemispheric connections by α-rhythm continuously decreased and reached normal values by the end of the treatment. In addition, a considerable decrease of intra-hemispheric connections by β-rhythm was observed immediately after the first administration of sodium bicyclo-[2.2.2]-octane-2-carboxylate.

Thus epilepsy patients displayed a decrease in coherence primarily within the δ- and θ-ranges, which reflected a diminishing of anomalous neuronal connections in the focus of paroxysmal activity.

ECGs were recorded before the beginning of the treatment, during the course of the study (on a regular basis), and immediately after the study had been completed. The majority of the patients did not show any changes in the heart activity. Normal sinus rhythm was seen in these patients. In the patients with extrasystolia and tachycardia, extrasystolia was not observed by the end of the first treatment month, while the heart rate decreased on average from 88/min to 80/min. In the patients with bradycardia, sinus rhythm dropped further.

In summary.
1) Sodium bicyclo-[2.2.2]-octane-2-carboxylate showed pronounced anti-convulsive activity in epilepsy patients. Statistically significant decrease in seizure frequency was observed in 73.3% of all cases. The majority of the patients experienced shorter, less severe and less frequent seizures.
2) Sodium bicyclo-[2.2.2]-octane-2-carboxylate proved to be an effective treatment of dysphoria or dysphoria-like conditions in 93.3% of all cases. In these patients, emotional distress diminished, accompanied by normalizing of the behavior and thinking rate.
3) Sodium bicyclo-[2.2.2]-octane-2-carboxylate did not cause any changes in blood and urine tests.
4) Sodium bicyclo-[2.2.2]-octane-2-carboxylate exhibited some effect on the heart.
5) During 10 weeks of sodium bicyclo-[2.2.2]-octane-2-carboxylate treatment, patients' behavior and the functions of major organs and systems were not negatively affected.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for reducing dysphoria and the number or strength of seizures in a human subject suffering from dysphoria and epilepsy, the method comprising the step of orally administering to the subject 50-1200 mg of the bicyclo-[2.2.2]-octane-2-carboxylate salt per day at least until the dysphoria and the number or strength of seizures in the human subject are reduced.

2. The method of claim 1, wherein the human subject is administered the 50-1200 mg of the bicyclo-[2.2.2]-octane-2-carboxylate salt per day for at least 60 days.

3. The method of claim 1, wherein the epilepsy is partial epilepsy.

4. The method of claim 1, wherein the bicyclo-[2.2.2]-octane-2-carboxylate salt is formulated for sustained or delayed release.

5. The method of claim 1, wherein the human subject also suffers from ethanol addiction and the bicyclo-[2.2.2]-octane-2-carboxylate salt is administered at least until ethanol craving and the number or strength of seizures in the subject is reduced.

6. The method of claim 1, wherein the human subject has an elevated liver function marker selected from the group consisting of AST, ALT, and bilirubin, and the bicyclo-[2.2.2]-octane-2-carboxylate salt is administered at least until the liver function marker and the number or strength of seizures in the subject is reduced.

7. The method of claim 1, wherein the human subject has an elevated erythrocyte sedimentation rate, and the bicyclo-[2.2.2]-octane-2-carboxylate salt is administered at least until the erythrocyte sedimentation rate and the number or strength of seizures in the subject is reduced.

* * * * *